United States Patent [19]

Daunter

[11] Patent Number: 4,959,216
[45] Date of Patent: Sep. 25, 1990

[54] CONTRACEPTIVE METHODS AND DELIVERY SYSTEMS THEREOF

[75] Inventor: Brian Daunter, Bellbowrie, Australia

[73] Assignee: University of Queensland, Queensland, Australia

[21] Appl. No.: 134,263

[22] Filed: Dec. 17, 1987

Related U.S. Application Data

[63] Continuation-in-part of Ser. No. 819,510, filed as PCT AU85/00081 on Apr. 17, 1985, as WO85/04798 on Nov. 7, 1985, abandoned.

[30] Foreign Application Priority Data

Apr. 19, 1984 [AU] Australia .................... PG4658

[51] Int. Cl.⁵ .................... A61K 33/34; A61M 31/00
[52] U.S. Cl. .................... 424/430; 128/832; 514/843; 424/425; 424/426
[58] Field of Search ............... 128/830, 832, 833, 834, 128/841; 424/430, 432, 433, 434, 425, 426; 514/843

[56] References Cited

U.S. PATENT DOCUMENTS

| | | | |
|---|---|---|---|
| 3,563,235 | 2/1971 | Zipper | 128/833 |
| 3,803,308 | 4/1974 | Zipper | 424/635 |
| 3,834,378 | 9/1974 | Lerner et al. | 128/833 |
| 3,934,580 | 1/1976 | Cournut | 128/833 |
| 3,957,975 | 5/1976 | Bohn et al. | 514/8 |
| 4,004,006 | 1/1977 | Shulman et al. | 424/245 |
| 4,040,417 | 8/1977 | Zipper | 128/833 |
| 4,252,787 | 2/1981 | Sherman et al. | 424/45 |
| 4,264,576 | 4/1981 | Zimmerman et al. | 424/432 |
| 4,387,094 | 6/1983 | Bagros | 514/843 X |
| 4,393,871 | 7/1983 | Vorhauer et al. | 128/833 |
| 4,553,972 | 11/1985 | Vickery | 128/833 X |
| 4,589,880 | 5/1986 | Dunn et al. | 128/832 |

FOREIGN PATENT DOCUMENTS

| | | |
|---|---|---|
| 85064/75 | 9/1975 | Australia . |
| 91319/82 | 6/1983 | Australia . |
| 125092 | 11/1984 | European Pat. Off. . |
| 2160063 | 5/1972 | Fed. Rep. of Germany . |
| 1375848 | 11/1974 | United Kingdom . |

OTHER PUBLICATIONS

D. P. Froman & R. J. Thurston, "Decreased Fertility Resulting from Treatment of Fowl Spermatozoa with Neuraminidase or Phospholipase C", *Poultry Science*, vol. 63, published 1984, pp. 2479–2482.

R. Rajan, A. R. Sheth & Shanta S. Rao, "Sialic Acid, Sialyltransferase and Neuraminidase Levels in Material Plasma, Urine and Lymphocytes During Pregnancy and Post Partum Period–A Longitudinal Study in Women", Europ. J. Obstet., *Gynec. Reprod. Biol.*, vol. 16, published 1983 (Elsevier Science Publishers B.V.), pp. 37–46.

*Primary Examiner*—Randolph A. Reese
*Assistant Examiner*—Jeffrey L. Thompson
*Attorney, Agent, or Firm*—Foley & Lardner, Schwartz, Jeffery, Schwaab, Mack, Blumenthal & Evans

[57] ABSTRACT

A contraceptive method for living animals (including human beings) can utilize a polyurethane or polyvinylacetate (PVA) disc as an inert carrier for contraceptive preparations, the disc being implanted before intercourse to engage the external os of the cervical canal. Preferred contraceptive preparations include (1) the copper (II) salt of ethylenediamine-tetraacetic acid (EDTACu) and L-L-ascorbic acid; (2) the sialic acid-removing enzyme neuraminidase; and (3) an asialoglycoprotein, such as asialofetuin. Of these preparations, which can be used separately or in any combination, the first two act on the cervical mucus to change it from the open cellular structure found at midcycle of the menstrual period to the closed cellular structure and thus form an impenetrable barrier for spermatozoa. The second and third preparations remove sialic acid from spermatozoa, the presence of which is necessary for successful fertilization.

28 Claims, 1 Drawing Sheet

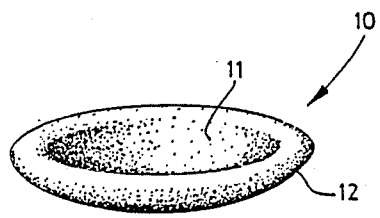
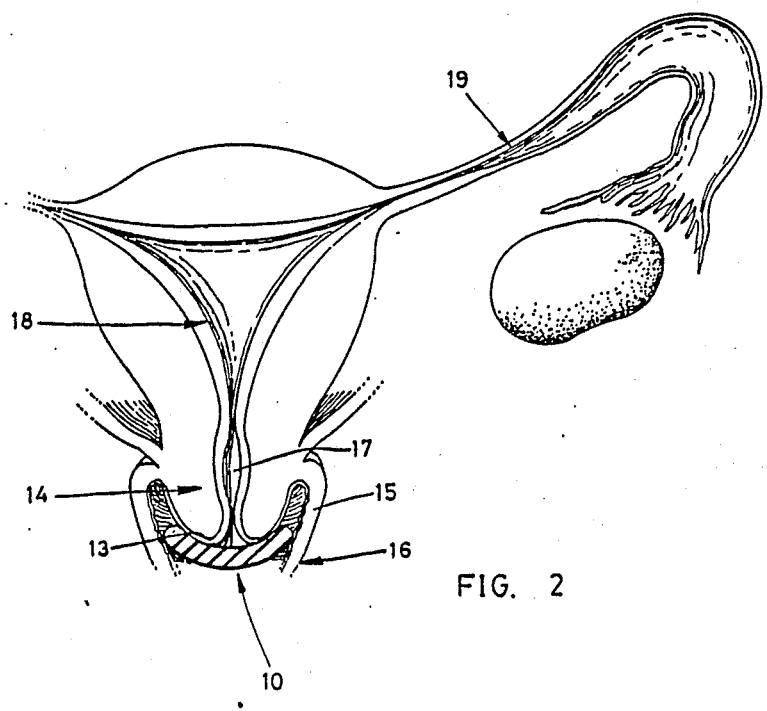

CONTRACEPTIVE METHODS AND DELIVERY SYSTEMS THEREOF

This is a continuation-in-part of Ser. No. 819,510, filed as PCT AU85/00081 on Apr. 17, 1985 published as WO85/04798 on Nov. 7, 1985, now abandoned.

BACKGROUND OF THE INVENTION (1) Field of the Invention

This invention relates to contraceptive preparations and methods for living animals (including human beings) and to delivery systems for the preparation.

(1) Prior Art

A report from the Royal College of General Practitioners in 1981 stated that evidence indicated women who had taken oral contraceptives had a 40% higher death rate than those who used other contraceptive methods. The high mortality rate appeared to be mainly due to diseases in the circulatory system in the over-35 age group. These findings give cause for concern. Indeed, many women have returned to traditional contraceptive methods as a result of the publicity given to the use of hormonal contraceptives.

SUMMARY OF THE INVENTION

It is an object of the present invention to provide a contraceptive method which acts at the level of the vagina and/or the cervical canal.

It is a preferred object to provide contraceptive preparations suitable for the method employing chemicals found naturally-occurring in the bodies of living animals.

It is a further preferred object to provide such preparations which appear to have no known or predictable side effects and which are non-hormonal and which cause no known disturbance to the menstrual cycle.

It is a still further preferred object to provide such preparations which can be easily self-administered and which are only used in the fertile phase of the menstrual cycle.

It is a still further preferred object to provide a simple, yet effective, delivery system for the preparations.

At the commencement of the menstrual cycle, it has been observed that the cervical mucus has a tight "honey-comb" or cellular structure (with a channel diameter of approximately 2–6 $\mu$m) which forms an impenetrable barrier to the spermatozoa. At midcycle, the cellular structure opens up and the diameter of the channels is in the range of approximately 30–35 $\mu$m, allowing the spermatozoa to pass through the mucus into the cervical cavity. After midcycle, the cellular structure again contracts to a channel diameter range of approximately 2–6 $\mu$m.

It is believed that before and after midcycle, the cellular structure is tightly bound together by copper ions cross-linking the terminal carboxylic acid groups of the sialic acid found on the branches of the glycoprotein chains forming the mucus.

The present inventor has now established that the cervical mucus can be made to close midcycle to form an impenetrable barrier to spermatozoa by the introduction into the vaginal and/or cervical regions of a metal ion which can complex with the mucus and cause it to resume the tight cellular structure.

Thus, according to a first aspect of the present invention, there is provided a method of contraception for a living animal, said method comprising introducing a contraceptive preparation into the vaginal and/or cervical regions of the female reproductive system, wherein said preparation includes a metal ion which can complex with the cervical mucus to form an impenetrable barrier to spermatozoa.

Conveniently, the metal ions can be produced in situ from a preparation which comprises a metal chelate and a suitable reducing agent.

Preferably, the metal chelate is copper (II) ethylenediamine-tetraacetic acid and the reducing agent is L-ascorbic acid. An advantage in using these two compounds is that both the $Cu^+$ ions (from the metal chelate) and the hydrogen peroxide (produced as a secondary product from the overall reaction of closing the mucus) are both toxic to spermatozoa.

Other metal cations which may be suitable for this aspect of the present invention are iron (divalent/trivalent) or other divalent/trivalent ions (for example, calcium, zinc and manganese).

It has also been established that in 40% of women with midcycle "hostile" mucus (i.e., mucus which immobilizes spermatozoa), the mucus is deficient in sialic acid. Reconstructing this mucus by the enzymatic addition of sialic acid removes the hostility. It appears that in such cases of infertility resulting from mucus deficient in sialic acid, that spermatozoal transferable sialic acid can also be depleted.

It particular, semen upon disposition in the vagina undergoes coagulation and then liquefaction to allow spermatozoa to escape into the neck of the uterus (cervical canal). The prevention of seminal plasma liquefaction will result in spermatozoal immobilization and then death due to the acidity of the vagina. The loss of spermatozoal transferable sialic acid, by supplying an acceptor molecule, will prevent any spermatozoa that survive from transferring their sialic acid to the zona pellucida of the ova, which is required for fertilization.

These results suggest that any compound which could remove sialic acid from the mucus or from spermatozoa during the midcycle ovulatory period may be useful as an intravaginal and/or intracervical contraceptive.

Therefore, according to a second aspect of the present invention, there is provided a method of contraception for a living animal, said method comprising introducing a contraceptive preparation in to the vaginal and/or cervical regions of the female reproductive system wherein:

said preparation comprises a compound capable of removing sialic acid from the cervical mucus.

Further, according to a third aspect of the present invention, there is provided a method of contraception for a livinq animal, said method comprising introducing a contraceptive preparation into the vaginal and/or cervical regions of the female reproductive system wherein:

said preparation comprises an acceptor for spermatozoal sialic acid to prevent penetration and fertilization of ova by the spermatozoa.

Preferably, the enzyme neuraminidase is used to remove the sialic acid from the cervical mucus and the spermatozoal transferable sialic acid is preferably depleted with an asialoglycoprotein, more preferably, asialofetuin.

The above three methods can be used in isolation or in any combination thereof. The contraceptive preparations may contain additional compounds which also may exhibit contraceptive properties. For example, they may be a spermotoxic agent, such as NONOX- YNOL 9 (product of Sigma Chemical Company, St. Louis, Mo. U.S.A.).

Any suitable delivery system can be used for positioning the contraceptive preparations of the present invention in the vaginal and/or cervical regions.

The preparation may be applied, e.g., in a foam, cream or gel; as a coating on condoms; by impregnation of vaginal/cervical inserts; by intracervical gelatin capsules or slow release intracervical capsules; or by implantation adjacent or into the cervical canal by a dispenser having a discharge nozzle adapted to engage the cervical canal.

The preferred form of delivery is in the form of a cap or disc adapted to engage the external os of the cervical canal (and which may also engage the vaginal wall), the cap or disc having a cellular structure to provide a matrix for the contraceptive preparation. Suitable materials for the cap or disc include polyurethane and polyvinylacetate (PVA). PVA is preferred as it is both inert and has a high absorptive and retention capacity. However, a currently available vaginal contraceptive sponge marketed under the name TODAY may also prove suitable.

BRIEF DESCRIPTION OF THE DRAWINGS

To enable the invention to be fully understood, a number of preferred embodiments will now be described with reference to the accompanying drawings, in which:

FIG. 1 is a perspective view of a PVA disc used to retain the contraceptive preparations of the invention; and FIG. 2 is a section view showing the PVA disc positioned in the vagina of the reproductive system of a human female.

DETAILED DESCRIPTION OF THE PREFERRED EMBODIMENTS

Referring to FIG. 1, the disc 10 is formed of polyvinylacetate and is concave in slope with a central depression 11 surrounded by a peripheral rim 12. For use in human females, the disc may be 4–5 cm in diameter and between 1–2 cm thick, the disc being arranged as shown in FIG. 1 to engage the external os 13 of the cervix 14 (and to preferably engage the adjacent wall 15 of the vagina 16). It will be readily apparent to the skilled addressee that any spermatozoa deposited in the vagina 16 by the male must pass through the disc 10 to enter the cervical canal 17 on their passage to the uterus 18 and fallopian tubes 19.

The PVA disc is an inert carrier with a high absorptive and retention capacity and the contraceptive compounds to be described are incorporated in the matrix provided by the disc and are activated by wetting with a small amount of water before the disc is implanted by the user using a finger. The spermatozoa and seminal plasma are absorbed by the disc and brought into contact with the contraceptive preparation.

The disc will be implanted by the female, e.g., up to 1 hour before sexual intercourse occurs.

Example 1

200 mg of the copper salt of ethylenediaminetetraacetic acid (EDTACu) and 80 mg of L-ascorbic acid are contained within the PVA disc 10. The overall reaction is as follows:

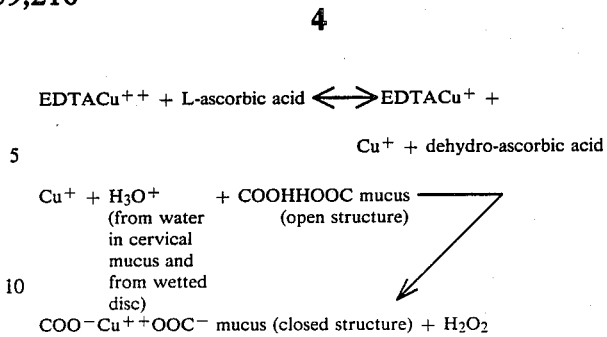

The system generates copper (I) ions within the matrix of the PVA disc upon wetting prior to implantation. The copper (I) ions complex the open structure mucus, in contact with the PVA disc, and will result in the closing of the mucus structure, preventing spermatozoal penetration.

The closing of the mucus structure has been confirmed by scanning electron microscopic examination. The copper ions are toxic to the spermatozoa and also cause reformation of the seminal plasma coagulum within the matrix of the disc. Thus the contraceptive action is four-fold, i.e., (1) preventing spermatozoal penetration of the cervical mucus by changing the structure of the mucus;
(2) trapping the spermatozoa in the matrix of the disc by the reformation of the coagulum;
(3) the spermatoxic nature of the copper (I) ions; and
(4) the spermatoxic nature of the hydrogen peroxide.

Example II 500 units of the enzyme neuraminidase is incorporated in the matrix of the PVA disc. The neuraminidase removes the sialic acid from the cervical mucus in contact with the disc and renders it "hostile" to the spermatozoa. The loss of the sialic acid from the mucus closes its open cellular structure which prevents spermatozoal penetration. The spermatozoa also transfer their sialic acid to the mucus. As sialic acid is required by spermatozoa to penetrate the ova to effect fertilization, any spermatozoa which do pass through the mucus will be incapable of fertilization.

Example III

Example I is modified by the addition of 200 mg of asialofetuin to the PVA disc. The asialofetuin does not act on the mucus but provides an acceptor for the transfer of the spermatozoal sialic acid to prevent fertilization of the ova by the spermatozoa.

Example IV

Example II is modified by the addition of the asialofetuin in the manner described in Example III.

Example V

The ETDACu and L-ascorbic acid of Example I and the neuraminidase of Example II are incorporated in the PVA disc to provide the different form of contraceptive action described above.

Example VI

Example V is modified by the addition of the asialofetuin of Example III.

It will be readily apparent to the skilled addressee that the present invention provides a simple, yet effective method of contraception at the midcycle of the menstrual period, which is the only time when conception can occur. The contraceptive preparations are non-toxic and have no known side effects and the use of a disc as an inert carrier therefore produces a simple yet effective delivery system wherein the disc can be implanted just before intercourse takes place.

Various changes and modifications may be made to the embodiments and examples described without departing from the scope of the present invention as defined in the appended claims.

What is claimed is:

1. A method of contraception for a living animal, said method comprising the step of introducing a contraceptive preparation into the vaginal and/or cervical regions of hte female reproductive system, wherein said contraceptive preparation comprises a chelate of a metal ion and a reducing agent, which metal ion can complex with the cervical mucus to form an impenetrable barrier to spermatozoa.

2. A method as claimed in claim 1, wherein the contraceptive preparation causes the open cellular structure of the cervical mucus, which allows spermatozoa to enter the cervical canal at the midcycle of the menstrual cycle, to become closed and form the impenetrable barrier.

3. A method as claimed in claim 2, wherein the channel diameter of the closed cellular structure of the cervical mucus is less than the diameter of the spermatozoa.

4. A method as claimed in claim 1, wherein the metal ion comprises at least one of a divalent and trivalent metal cation.

5. A method as claimed in claim 4, wherein the metal cation is selected from the group consisting of copper, iron, calcium, zinc and manganese.

6. A method as claimed in claim 1, wherein the metal chelate is copper (II) ethylenediaminetetraacetic acid and the reducing agent is L-ascorbic acid.

7. A method as claimed in claim 1, wherein the contraceptive preparation further comprises a compound capable of removing sialic acid from the cervical mucus.

8. A method as claimed in claim 7, wherein the compound is the enzyme neuraminidase.

9. A method as claimed in claim 1, wherein the contraceptive preparation further comprises an acceptor for spermatozoal sialic acid to prevent penetration and fertilization of ova by the spermatozoa.

10. A method as claimed in claim 9, wherein the acceptor is an asialoglycoprotein.

11. A method as claimed in claim 10, wherein the asialoglycoprotein is asialofetuin.

12. A method as claimed in claim 1, wherein the contraceptive preparation further comprises a spermatoxin.

13. A method as claimed in claim 12, wherein the spermatoxin is polyethoxyethylene (9)-nonytphenyl ether.

14. A method as claimed in claim 1, wherein the contraceptive preparation is combined with an inert carrier which comprises a foam, cream or gel, a coating on a condom, or a vaginal or cervical insert.

15. A method as claimed in claim 14, wherein the inert carrier is a vaginal or cervical insert which comprises a cap or disc of cellular material to support the contraceptive preparation.

16. A method as claimed in claim 15, wherein the cap or disc is engageable with the wall of the vagina adjacent the cervix.

17. A method as claimed in claim 15, wherein the cellular material is polyvinylacetate.

18. A contraceptive preparation for living animals to be introduced into the vaginal and/or cervical regions of the female reproductive system, said contraceptive preparation comprising (i) a metal chelate and (ii) a suitable reducing agent, wherein said preparation, when introduced into said regions, releases metal ions which complex with the cervical mucus to form an impenetrable barrier to spermatozoa.

19. A contraceptive preparation as claimed in claim 18, wherein the metal chelate comprises at least one of a divalent and a trivalent metal cation.

20. A contraceptive preparation as claimed in claim 19, wherein the metal cation is selected from the group consisting of copper, iron, calcium, zinc and manganese.

21. A contraceptive preparation as claimed in claim 18, wherein the metal chelate is copper (II) ethylenediamine-tetraacetic acid and the reducing agent is L-ascorbic acid.

22. A contraceptive preparation as claimed in claim 18, further comprising a compound capable of removing sialic acid from the cervical mucus.

23. A contraceptive preparation as claimed in claim 22, wherein the compound is the enzyme neuraminidase.

24. A contraceptive preparation as claimed in claim 18, further comprising an acceptor for spermatozoal sialic acid to prevent penetration and fertilization of ova by the spermatozoa.

25. A contraceptive preparation as claimed in claim 24, where in the acceptor is an asialoglycoprotein.

26. A contraceptive preparation as claimed in claim 25, wherein asialoglycoprotein is asialofetuin.

27. A preparation as defined in claim 18, additionally comprising a spermatoxin.

28. A preparation as defined in claim 18, wherein the spermatoxin is polyethoxyethylene (9)-nonylphenyl ether.

* * * * *